(12) United States Patent
Hart

(10) Patent No.: US 8,968,370 B2
(45) Date of Patent: Mar. 3, 2015

(54) METHOD AND APPARATUS FOR DENS FRACTURE FIXATION

(75) Inventor: Robert Alan Hart, Portland, OR (US)

(73) Assignee: Oregon Health & Science University, Portland, OR (US)

( * ) Notice: Subject to any disclaimer, the term of this patent is extended or adjusted under 35 U.S.C. 154(b) by 352 days.

(21) Appl. No.: 12/746,070

(22) PCT Filed: Dec. 19, 2007

(86) PCT No.: PCT/US2007/088128
§ 371 (c)(1),
(2), (4) Date: Jun. 3, 2010

(87) PCT Pub. No.: WO2009/078877
PCT Pub. Date: Jun. 25, 2009

(65) Prior Publication Data
US 2010/0268230 A1    Oct. 21, 2010

(51) Int. Cl.
*A61B 17/80*    (2006.01)
*A61B 17/70*    (2006.01)
*A61B 17/86*    (2006.01)

(52) U.S. Cl.
CPC .......... *A61B 17/7059* (2013.01); *A61B 17/863* (2013.01)
USPC ............ 606/286; 606/70; 606/282; 606/246; 606/279

(58) Field of Classification Search
USPC ............................ 606/70, 286, 246, 279, 282
See application file for complete search history.

(56) References Cited

U.S. PATENT DOCUMENTS

| | | |
|---|---|---|
| 4,135,506 A | 1/1979 | Ulrich |
| 5,147,361 A | 9/1992 | Ojima et al. |
| 5,318,567 A | 6/1994 | Vichard |
| 5,743,914 A | 4/1998 | Skiba |
| 5,871,486 A | 2/1999 | Huebner et al. |
| 5,954,722 A | 9/1999 | Bono |
| 7,186,256 B2 | 3/2007 | Michelson |
| 7,235,079 B2 | 6/2007 | Jensen et al. |
| 2004/0225290 A1* | 11/2004 | Ferree .............................. 606/61 |
| 2005/0101961 A1 | 5/2005 | Huebner et al. |
| 2005/0131413 A1 | 6/2005 | O'Driscoll et al. |
| 2005/0192578 A1 | 9/2005 | Horst |

(Continued)

OTHER PUBLICATIONS

Jenkins, Jeffrey D. et al. "A Clinical Comparison of One- and Two-Screw Odontoid Fixation," Journal of Neurosurgery, Sep. 1998, vol. 89, pp. 366-370, American Association of Neurosurgeons, 1224 Jefferson Park Avenue, Suite 450, Charlottesville, Virginia 22903.

(Continued)

*Primary Examiner* — Andrew Yang
*Assistant Examiner* — Olivia C Chang
(74) *Attorney, Agent, or Firm* — Schwabe, Williamson & Wyatt

(57) ABSTRACT

Embodiments of the present invention provide methods, apparatuses, and systems for fixing dens fractures. The mode of failure for screw fixation of C2 dens fractures is often via cut-out at the anterior body. In an embodiment, securing a plate, such as a locking plate, to the anterior surface of the vertebra attached directly to an interfragmentary screw may reduce potential for anterior screw cut-out and improve construct strength. Plate supplementation of anterior screw fixation of Type II dens fractures thus improves construct strength and changes the failure mechanism from anterior screw cut-out to posterior displacement of the screw, thus improving clinical outcomes for these fractures.

15 Claims, 4 Drawing Sheets

(56) References Cited

U.S. PATENT DOCUMENTS

| | | | | |
|---|---|---|---|---|
| 2005/0240185 | A1* | 10/2005 | Boomer et al. | 606/69 |
| 2006/0084989 | A1 | 4/2006 | Dickinson et al. | |
| 2006/0173462 | A1 | 8/2006 | Kay et al. | |
| 2006/0195085 | A1 | 8/2006 | Happonen et al. | |
| 2006/0229622 | A1* | 10/2006 | Huebner et al. | 606/73 |
| 2007/0055252 | A1 | 3/2007 | Blain et al. | |
| 2007/0123879 | A1 | 5/2007 | Songer et al. | |

OTHER PUBLICATIONS

Etter, Christian et al., "Direct Anterior Fixation of Dens Fractures With a Cannulated Screw System," Spine, 1991, vol. 16, No. 3 Supplement, S25-S32, Lippincott Williams & Wilkins, Two Commerce Square, 2001 Market Street Philadelphia, PA 19103.

Morandi, Xavier et al., "Anterior Screw Fixation of Odontoid Fractures," Surg Neurol., 1999, vol. 51, pp. 236-240.

Dickman, Curtis A., "Cannulated Screws for Odontoid Screw Fixation and Atlantoaxial Transarticular Screw Fixation," Journal of Neurosurgery, Dec. 1995, vol. 83, pp. 1095-1100, American Association of Neurosurgeons, 1224 Jefferson Park Avenue, Suite 450, Charlottesville, Virginia 22903.

Aebi, Max, et al., "Fractures of the Odontoid Process: Treatment with Anterior Screw Fixation," Spine, 1989, vol. 14, No. 10, pp. 1065-1070, Lippincott Williams & Wilkins, Two Commerce Square, 2001 Market Street, Philadelphia, PA 19103.

Apfelbaum, Ronald I. et al., "Direct Anterior Screw Fixation for Recent and Remote Odontoid Fractures," Journal of Neurosurgery, Oct. 2000, vol. 93, pp. 227-236, American Association of Neurosurgeons, 1224 Jefferson Park Avenue, Suite 450, Charlottesville, Virginia 22903.

Etebar, Shahin, et al., "Failure of Transodontoid Screw Fixation," Journal of Neurosurgery, Jan. 1998, vol. 88, pp. 158-160, American Association of Neurosurgeons, 1224 Jefferson Park Avenue, Suite 450, Charlottesville, Virginia 22903.

Doherty, Brian J., et al., "A Biomechanical Study of Odontoid Fractures and Fracture Fixation," Spine, 1993, vol. 18, No. 2, pp. 178-184, Lippincott Williams & Wilkins, Two Commerce Square, 2001 Market Street, Philadelphia, PA 19103.

Magee, William, et al., "Biomechanical Comparison of a Fully Threaded, Variable Pitch Screw and a Partially Threaded Lag Screw for Internal Fixation of Type II Dens Fractures," Spine, 2007, vol. 32, No. 17, pp. E475-E479, Lippincott Williams & Wilkins, Two Commerce Square, 2001 Market Street, Philadelphia, PA 19103.

Amling, Michael, et al., "Structural Heterogeneity Within the Axis: the Main Cause in the Etiology of Dens Fractures," Journal of Neurosurgery, Aug. 1995, vol. 83, pp. 330-335, American Association of Neurosurgeons, 1224 Jefferson Park Avenue, Suite 450, Charlottesville, Virginia 22903.

Amling, Michael, et al., The Microarchitecture of the Axis as the Predisposing Factor for Fracture of the Base of the Odontoid Process., The Journal of Bone and Joint Surgery, Incorporated, Dec. 1994, vol. 76-A, No. 12, pp. 1840-1846, Ovid Technologies, Inc., 333 Seventh Avenue, 20th Floor, New York, NY 10001.

Heggeness, Michael H., et al., "The Trabecular Anatomy of the Axis," Spine, 1993, vol. 18, No. 14, pp. 1945-1949, Lippincott Williams & Wilkins, Two Commerce Square, 2001 Market Street, Philadelphia, PA 19103.

Korres, Dimitrios, et al., "Structural Properties of the Axis Studied in Cadaveric Specimens," Clinical Orthopaedics and Related Research, Jan. 2004, vol. 418, pp. 134-140, Lippincott Williams & Wilkins, Two Commerce Square, 2001 Market Street, Philadelphia, PA 19103.

\* cited by examiner

METHOD AND APPARATUS FOR DENS FRACTURE FIXATION

TECHNICAL FIELD

Embodiments of the present invention relate to the field of orthopedics, and, more specifically, to a method and apparatus for dens fracture fixation.

BACKGROUND

Fractures of the dens (odontoid process) of the second cervical vertebra (C2) may result from severe forces, including rotation, across the cervical spine. Dens fractures may be classified according to the scheme of Anderson and D'Alonzo. Type I fractures occur at the tip of the dens. Type II fractures occur at the base of the dens without extension to the body of C2. Type III fractures occur in the body of C2.

Anderson and D'Alonzo Type II dens fractures are often fixed using a single cannulated lag screw and washer. While several authors have reported excellent results with this technique, pseudarthrosis rates approaching 20% or more have also been noted to occur. The mode of failure in patients progressing to pseudarthrosis appears to occur more frequently due to loss of fixation at the C2 body than within the dens itself.

Biomechanical studies using cadaveric models of Type II dens fractures fixed with a single cannulated lag screw have also demonstrated failure via anterior cut-out of the screw through the C2 body rather than through loss of fixation within the dens. This failure mode is consistent with the osseous architecture of the body of the axis vertebra, which has been shown to have a decreased cortical thickness and decreased density of trabecular bone relative to the dens itself.

A fully threaded variable pitch screw has recently been demonstrated to be a biomechanically favorable alternative to a partially threaded lag screw with a washer for fixation of Type II dens fractures. However, the reported mechanism of failure for both constructs was consistently via anterior cut-out of the screw through the body of C2.

BRIEF DESCRIPTION OF THE DRAWINGS

Embodiments of the present invention will be readily understood by the following detailed description in conjunction with the accompanying drawings. Embodiments of the invention are illustrated by way of example and not by way of limitation in the figures of the accompanying drawings.

DETAILED DESCRIPTION OF EMBODIMENTS OF THE INVENTION

Figure 1:
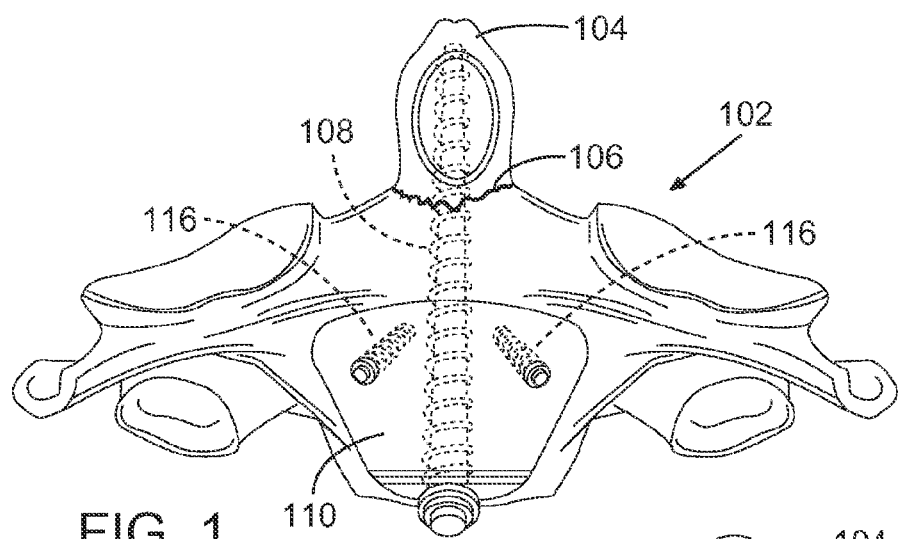
FIGS. 1, 2, 3, and 4 illustrate a fixation plate in various views secured to a vertebra (FIGS. 1 and 2) and separate (FIGS. 3 and 4) in accordance with various embodiments of the present invention.

In the following detailed description, reference is made to the accompanying drawings which form a part hereof, and in which are shown by way of illustration embodiments in which the invention may be practiced. It is to be understood that other embodiments may be utilized and structural or logical changes may be made without departing from the scope of the present invention. Therefore, the following detailed description is not to be taken in a limiting sense, and the scope of embodiments in accordance with the present invention is defined by the appended claims and their equivalents.

Various operations may be described as multiple discrete operations in turn, in a manner that may be helpful in understanding embodiments of the present invention; however, the order of description should not be construed to imply that these operations are order dependent.

The description may use perspective-based descriptions such as up/down, back/front, and top/bottom. Such descriptions are merely used to facilitate the discussion and are not intended to restrict the application of embodiments of the present invention.

The terms "coupled" and "connected," along with their derivatives, may be used. It should be understood that these terms are not intended as synonyms for each other. Rather, in particular embodiments, "connected" may be used to indicate that two or more elements are in direct physical or electrical contact with each other. "Coupled" may mean that two or more elements are in direct physical or electrical contact. However, "coupled" may also mean that two or more elements are not in direct contact with each other, but yet still cooperate or interact with each other.

For the purposes of the description, a phrase in the form "A/B" or in the form "A and/or B" means (A), (B), or (A and B). For the purposes of the description, a phrase in the form "at least one of A, B, and C" means (A), (B), (C), (A and B), (A and C), (B and C), or (A, B and C). For the purposes of the description, a phrase in the form "(A)B" means (B) or (AB) that is, A is an optional element.

The description may use the phrases "in an embodiment," or "in embodiments," which may each refer to one or more of the same or different embodiments. Furthermore, the terms "comprising," "including," "having," and the like, as used with respect to embodiments of the present invention, are synonymous.

In various embodiments of the present invention, methods, apparatuses, and systems for fixing dens fractures are provided. The mode of failure for screw fixation of C2 dens fractures is often via cut-out at the anterior body. In an embodiment of the present invention, securing a plate, such as a locking plate, to the anterior surface of the vertebra attached to, or secured in part by, an interfragmentary screw may reduce the potential for anterior screw cut-out and may improve construct strength. In accordance with an embodiment, plate supplementation of anterior screw fixation of Type II dens fractures improves construct strength and changes the failure mechanism from anterior screw cut-out to posterior displacement of the screw, thus improving clinical outcomes for these fractures.

In embodiments, a variety of interfragmentary screws may be utilized, including fully or partially threaded, headed or headless, uniform or variable pitch, locking or non-locking, or screws having various combinations thereof. For the purposes of describing embodiments of the invention, the term "interfragmentary" refers to a device, such as a screw, that crosses a fracture site in the bone interior. An exemplary interfragmentary screw may be seen in FIGS. 1, 2, 5, and 6 as the screw is inserted into the body of the dens and across the fracture site to provide fixation of and support to the healing dens.

In an exemplary embodiment, the present invention may be utilized to fix dens fractures of the C2 vertebra. Dens fractures that may be fixed in accordance with embodiments of the present invention include Anderson and D'Alonzo Type I, Type II, and Type III fractures. Type II fractures are of particular interest because such fractures are prone to pseudarthrosis unless sufficient stabilization of the fracture site is provided.

Thus, an embodiment of the present invention provides a vertebral fixation plate, comprising a primary plate body having a longitudinal axis and at least one securing screw hole configured to accept a securing screw to secure the primary plate body to an anterior surface of a vertebra, and a base region having a screw hole configured to accept a screw to secure the base region to the vertebra, wherein the base region forms an angle with respect to the longitudinal axis of the primary plate body. In a specific embodiment, a vertebral fixation plate is provided in which the primary plate body comprises a shoulder region and a waist region, the waist region being coupled at one end to the shoulder region and at an opposite end to the base region, wherein the waist region tapers along at least a portion thereof between the shoulder region and the base region. In embodiments, fixation constructs including a fixation plate and various screws, as well as methods of fixing dens fractures, are also provided.

For the purposes of describing embodiments of the present invention, the term "tapers" refers to a transition from a wider size/profile to a more narrow size/profile, whether in a straight line, curved, uniform, or varying along the length of the tapering region.

For the purposes of describing embodiments of the present invention, the terms "fixation," "fixing," or the like, refer to the stabilization of some or all of the parts of a fractured bone.

For the purposes of describing embodiments of the present invention, the term "locking screw" means a screw that has a mechanism for rigid or substantially rigid engagement with a corresponding screw hole in a plate. For the purposes of describing embodiments of the present invention, the term "locking plate" refers to a plate that has a mechanism for rigid or substantially rigid engagement with a corresponding screw. For the purposes of describing embodiments of the present invention, the term "locking screw hole" refers to a screw hole that has a mechanism for rigid or substantially rigid engagement with a corresponding screw.

FIGS. 1, 2, 3, and 4 illustrate a securing plate in various views secured to a vertebra (FIGS. 1 (coronal view) and 2 (sagittal view)) and separate (FIGS. 3 and 4) in accordance with various embodiments of the present invention. FIG. 1 shows a coronal view of C2 vertebra 102 with dens 104 exhibiting fracture 106. Fracture 106 is fixed using an interfragmentary screw 108 secured in vertebra 102 through plate 110. As shown, interfragmentary screw 108 resides in dens 104 without penetrating the apical cortex (tip) of dens 104. In addition, plate 110 is secured to a single vertebra (vertebra 102) without spanning a disk space and thus without contacting or being secured to the adjacent vertebra, thus allowing for a relatively small implant size.

Plate 110 is provided with a screw hole 112 adapted for passage of interfragmentary screw 108. In an embodiment, screw hole 112 may be provided with threads that correspond to the threads on the shaft of interfragmentary screw 108. In an embodiment, screw hole 112 may be provided with features to lock interfragmentary screw 108 in place and/or in a desired position, or it may be adapted for passage of interfragmentary screw 108. In embodiments, interfragmentary screw 108 may be used with or without a washer.

Plate 110 is also provided with two securing screw holes 114 for passage of securing screws 116. Screw holes 114 may be provided with features to lock securing screws 116 in place, or they may be adapted for passage of securing screws 116, whether or not a washer is also used. While plate 110 is shown with two securing screw holes 114, plate 110 may be provided with any suitable number of securing screw holes, including 1, 2, 3, 4, or more. In an embodiment, since the C2 vertebra may not be able to handle the insertion of a large number of screws due to the size and construction of the bone, the relatively small size of plate 110 may be beneficial in that only 1 or 2 securing screws may be needed to secure plate 110 to vertebra 102. As mentioned above, securing screw holes 114 and screws 116 may each independently provide any suitable securing mechanism, such as a locking screw/plate construct, as long as the securing mechanism(s) allows plate 110 to be secured to vertebra 102. In addition, securing screw holes 114 may be oriented to provide various predetermined angles of approach of securing screws 116, including angles for which securing screws 116 converge (point relatively toward each other as opposed to inserted in parallel) or diverge (point relatively away from other as opposed to inserted in parallel). In an embodiment, utilizing a plurality of securing screws in which at least two screws are inserted in a non-parallel fashion may further increase the construct strength.

Plate 110 is shown with an advantageous configuration contoured to vertebra 102. In an embodiment, anatomically pre-contoured plates may require little to no bending during implantation thus reducing surgical time and increasing ease of fit. In an embodiment, however, a plate, whether pre-contoured or not, may be bent or fit during implantation. Plate 110 has a relatively wide shoulder region 118, sized to fit vertebra 102 and provide construct strength. Coupled to shoulder region 118 is a narrower waist region 120, which is tapered to fit vertebra 102. In an embodiment, securing screw holes 114 may be located in shoulder region 118, but, in other embodiments, securing screw holes 114 may be located in shoulder region 118 and/or waist region 120. Shoulder region 118 and/or waist region 120 may also exhibit a transverse curvature (see for example FIGS. 2 and 4) to better conform to the shape of vertebra 102. Collectively, shoulder region 118 and waist region 120 may be referred to as the primary plate body. Waist region 120 is further coupled to base 122 which may be bent or curved at an angle to fit vertebra 102 and allow for proper alignment of screw hole 112, and thus for insertion of interfragmentary screw 108, so that interfragmentary screw 108 may be inserted in dens 104. In an embodiment, waist region 120 provides a gradual tapering of plate 110 from shoulder region 118 to base 122. Such tapering may be uniform or may vary, and may form a straight line, or may be curved.

Figure 5:
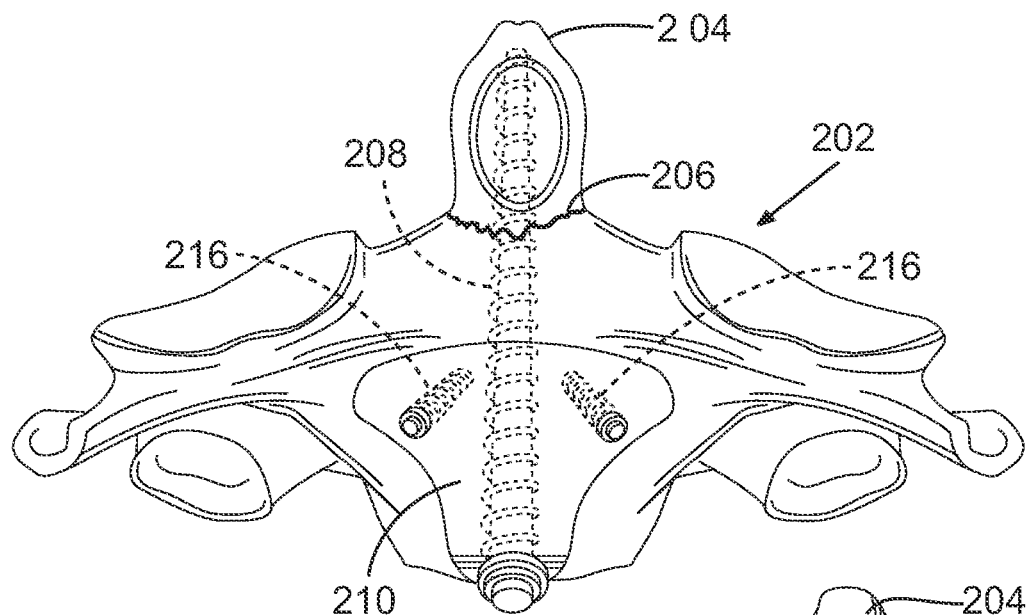
FIGS. 5, 6, 7, and 8 illustrate an alternative fixation plate in various views secured to a vertebra (FIGS. 5 and 6) and separate (FIGS. 7 and 8) in accordance with various embodiments of the present invention.
Figure 6:
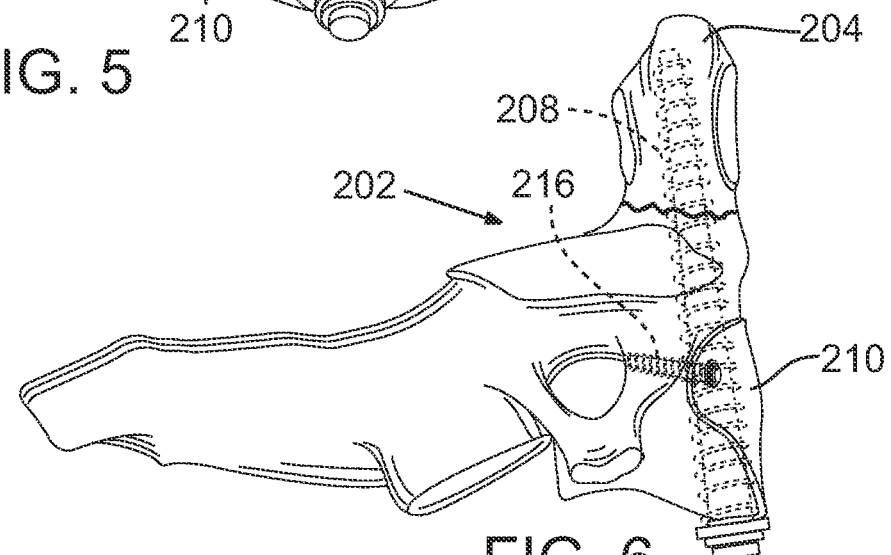
Figure 7:
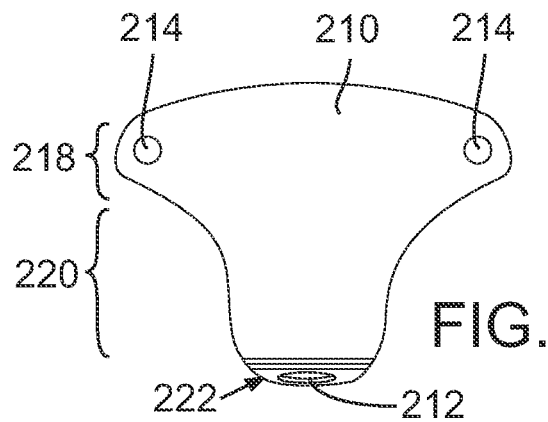
Figure 8:
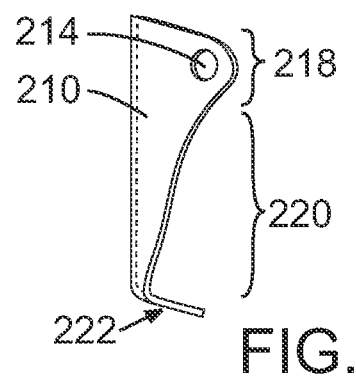

FIGS. 5, 6, 7, and 8 illustrate a securing plate in various views secured to a vertebra (FIGS. 5 (coronal view) and 6

Figure 2:
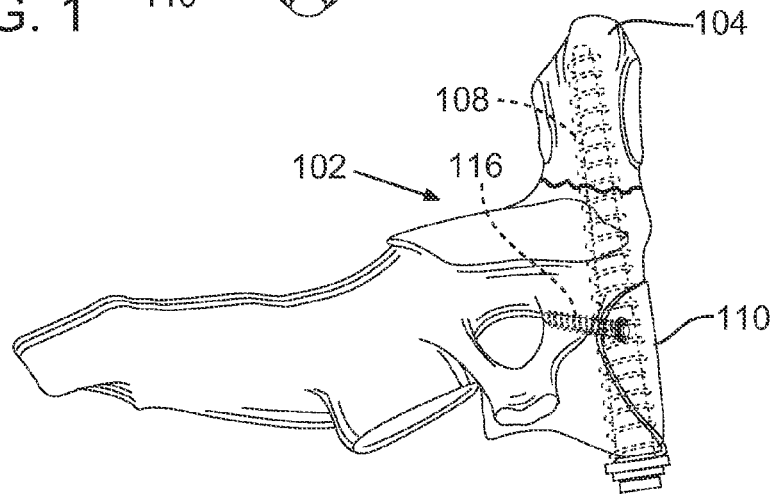
Figure 3:
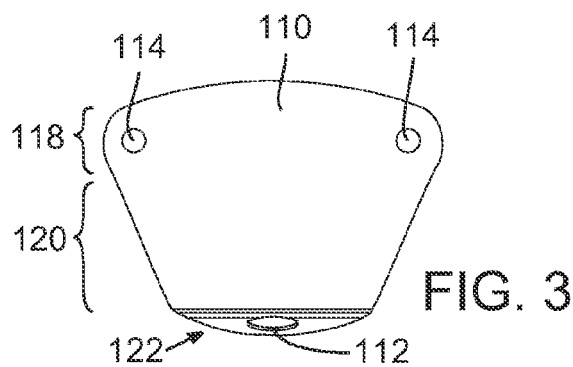
Figure 4:
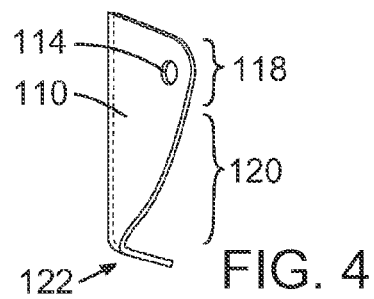

(sagittal view)) and separate (FIGS. 7 and 8) in accordance with various embodiments of the present invention. FIG. 2 shows a coronal view of C2 vertebra 202 with dens 204 exhibiting fracture 206. Fracture 206 is fixed using an interfragmentary screw 208 secured in vertebra 202 through plate 210. As shown, interfragmentary screw 208 resides in dens 204 without penetrating the apical cortex (tip) of dens 204. In addition, plate 210 is secured to a single vertebra (vertebra 202) without spanning a disk space thus allowing for a relatively small implant size.

Plate 210 is provided with a screw hole 212 adapted for passage of interfragmentary screw 208. In an embodiment, screw hole 212 may be provided with threads that correspond to the threads on the shaft of interfragmentary screw 208. In an embodiment, screw hole 212 may be provided with features to lock interfragmentary screw 208 in place and/or in a desired position, or it may be adapted for passage of interfragmentary screw 208, whether in use with or without a washer.

Plate 210 is also provided with two securing screw holes 214 for passage of securing screws 216. Screw holes 214 may be provided with features to lock securing screws 216 in place, or they may be adapted for passage of securing screws 216, whether in use with or without a washer. While plate 210 is shown with two securing screw holes 214, plate 210 may be provided with any suitable number of securing screw holes, including 1, 2, 3, 4, or more. In an embodiment, since the C2 vertebra may not be able to handle the insertion of a large number of screws, the relatively small size of plate 210 may be beneficial in that only 1 or 2 securing screws may be needed to secure plate 210 to vertebra 202. As mentioned above, securing screw holes 214 and screws 216 may each independently provide any suitable securing mechanism as long as the securing mechanism(s) allows plate 210 to be secured to vertebra 202. In addition, securing screw holes 214 may be oriented to provide various predetermined angles of approach of securing screws 216, including angles for which securing screws 216 converge (point relatively toward each other as opposed to inserted in parallel) or diverge (point relatively away from other as opposed to inserted in parallel). In an embodiment, utilizing a plurality of securing screws in which at least two screws are inserted in a non-parallel fashion may further increase the construct strength.

Plate 210 is shown with an advantageous configuration contoured to vertebra 202. In an embodiment, anatomically pre-contoured plates require little to no bending during implantation thus reducing surgical time and increasing ease of fit. In an embodiment, however, a plate, whether pre-contoured or not, may be bent or fit during implantation. Plate 210 has a relatively wide shoulder region 218, sized to fit vertebra 202 and provide construct strength. Coupled to shoulder region 218 is a narrower waist region 220, which is curved to fit vertebra 202. In an embodiment, securing screw holes 214 may be located in shoulder region 218, but, in other embodiments, securing screw holes 214 may be located in shoulder region 218 and/or waist region 220. Shoulder region 218 and/or waist region 220 may also exhibit a transverse curvature (see for example FIGS. 6 and 8) to better conform to the shape of vertebra 202. Collectively, shoulder region 218 and waist region 220 may be referred to as the primary plate body. Waist region 220 is further coupled to base 222 which is bent or curved at an angle to fit vertebra 202 and allow for proper alignment of screw hole 212 and thus for insertion of interfragmentary screw 108. In an embodiment, waist region 220 provides a curved and gradual tapering of plate 210 from shoulder region 218 to base 222. Such tapering may be uniform or may vary. In an embodiment, waist region 220 may curve for all or part of the distance between shoulder region 218 and base 222.

In the embodiments discussed above, the base region may form an angle with respect to a longitudinal axis of the primary plate body. In an embodiment, the angle is formed by a bend or curve at the lower portion of the plate toward the vertebra so that the entire plate at least partially conforms to the vertebra. This angle further allows for the screw hole in the base region to be aligned with the lower anterior portion of the C2 vertebra and to be aligned with the dens such that a screw inserted through the screw hole may be inserted in the C2 vertebra and into the dens. In embodiments, a suitable angle may be approximately 45-135°, such as approximately 80-100°.

In the embodiments shown in FIGS. 1-8, the wider shoulder region and securing screw orientation provides for the mechanical strength of the construct to be focused at the upper region of the construct. In an embodiment, the narrow waist allows the plate to conform to the shape of the vertebra. Further, the relatively narrow base allows the plate to conform to the shape of the vertebra and maintains the plate in a position away from the spinal disc between C2 and C3.

In accordance with an exemplary embodiment, sixteen fresh frozen human cadaveric C2 vertebrae were used as a model of a Type II dens fracture. Specimens were randomly allocated to fixation either by a fully-threaded variable pitch screw (FTVPS) alone or by an implant consisting of a FTVPS and a locking plate (a locking plate/screw construct (LPC)) by an attached anterior locking plate in accordance with an embodiment of the invention (as shown in FIGS. 1 and 2). Age and dual electron x-ray absorptiometry (DEXA) estimates of bone mineral density were recorded for each specimen.

Specimens were drilled over a guide wire using a 2.7 mm cannulated drill passing from the anterior, inferior body of C2 to the tip of the dens without penetration of the apical cortex. A transverse osteotomy was then made at the base of the dens using a two millimeter oscillating saw to simulate a Type II dens fracture. The osteotomies were reapproximated and instrumented with either an appropriate length FTVPS (Acutrak, Acumed LLC, Hillsboro, Oreg.) or a FTVPS in conjunction with an attachable locking plate. All FTVPS's were implanted without perforating the apical cortex of the dens. Anterior-posterior and lateral radiographs of each specimen were taken to confirm osteotomy reduction and screw position.

Crossed K-wires were placed through the spinous processes and laminae and the posterior portions of each specimen were potted in a polymethylmethacrylate base. Specimens were tested on a materials testing machine (Instron Corp., Norwood, Mass.). A static, posteriorly-directed force was applied to the anterior surface of the dens via a displacement-control paradigm at a rate of 5 mm/min. Load versus displacement data were collected at a frequency of 10.42 Hz. Specimens were loaded until gross failure of the construct was observed.

Construct stiffness was calculated from the slope of the initial linear portion of the load-displacement curve. Construct failure was identified by the first change in slope from a positive to a negative value in the load-displacement curve. Mean values for stiffness and load to failure were calculated for the FTVPS and LPC groups and compared using a two-tailed t-test. Mechanism of failure was determined for each specimen by a combination of direct visual and radiographic examination.

The mean age for FTVPS specimens was 55 years (range 33-75 years) compared to 52 years (range 21-78 years) for the LPC group. The mean bone mineral density for the FTVPS group was $0.203\pm0.041$ g/cm$^2$ compared to $0.195\pm0.033$ g/cm$^2$ for the LPC group. These values were not statistically different ($p=0.67$).

Figure 9:
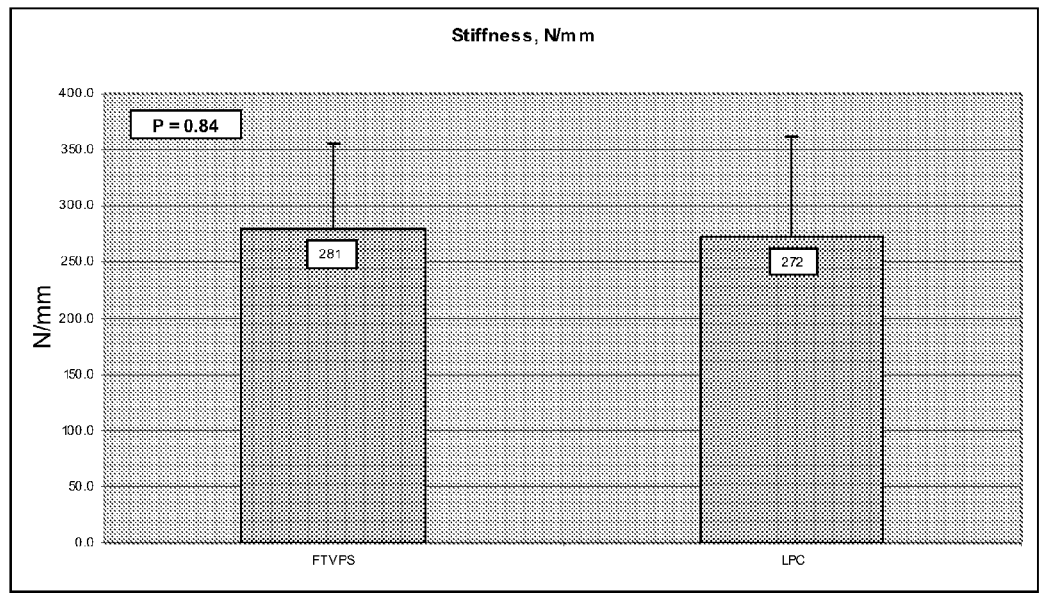
FIG. 9 shows a comparison of mean stiffness (N/mm) for fully-threaded variable pitch screws (FTVPS) alone and locking plate/screw (LPC) constructs in accordance with various embodiments of the present invention; p-value is for a two-tailed t-test.
Figure 10:
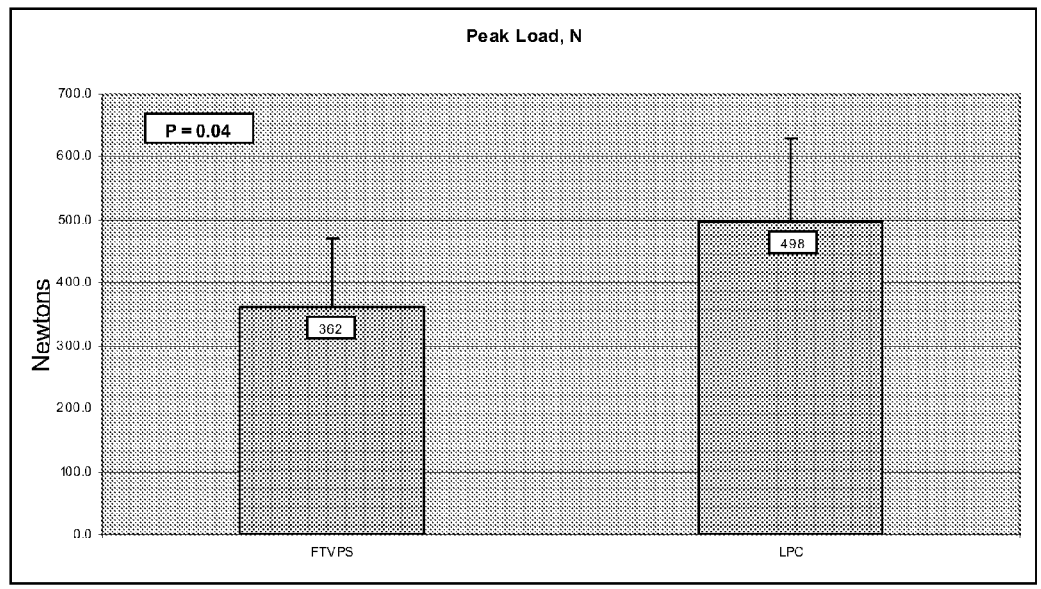
FIG. 10 shows a comparison of mean peak load (N) for fully-threaded variable pitch screws (FTVPS) alone and locking plate/screw (LPC) constructs in accordance with various embodiments of the present invention; p-value is for a two-tailed t-test.
Figure 11A:
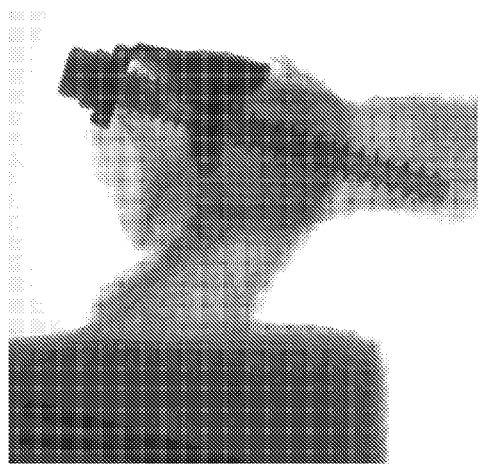
FIGS. 11A, 11B, 11C, and 11D are radiographs demonstrating LPC (11A) and FTVPS (11B) positioning before testing; the mechanism of failure for the LPC consistently occurred due to compression of cancellous bone posterior to the screw (11C); and failure of the FTVPS was via cut-out of the screw through the anterior aspect of the body of the axis (11D).
Figure 11B:
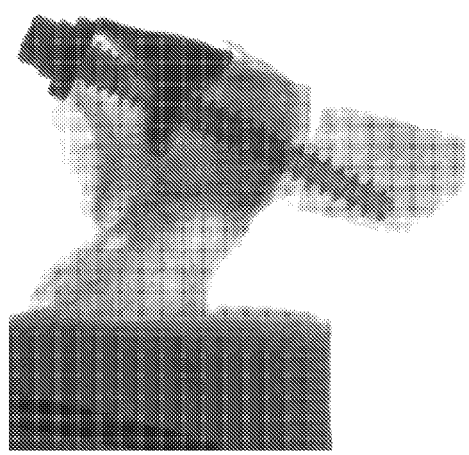
Figure 11C:
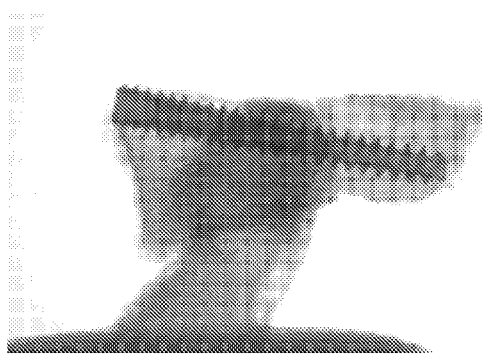
Figure 11D:
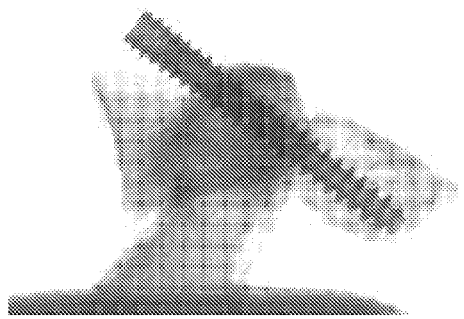

The mean stiffness for the FTVPS construct was $281\pm76$ N/mm compared to $272\pm89$ N/mm for the LPC group. This difference was also not statistically significant ($p=0.84$; FIG. 9). The mean load to failure for the FTVPS construct was $362\pm109$ compared to $498\pm133$ N for the LPC group. This difference was statistically significant ($p=0.04$; FIG. 10).

The mechanism of failure for all eight FTVPS constructs was via cut-out of the screw through the anterior body of C2. In contrast, the mechanism of failure for the LPC constructs was consistently via compression of cancellous bone posterior to the FTVPS. Radiographs of typical examples of pre- and post-failure specimens shown in FIGS. 11A, 11B, 11C, and 11D illustrate this description of the failure modes.

The exemplary results above demonstrate that use of an attachable locking plate with an interfragmentary screw for anterior screw fixation of Type II dens fractures significantly increases load to failure in extension load testing. In addition, construct failure by anterior C2 body cut-out was successfully eliminated.

Although certain embodiments have been illustrated and described herein for purposes of description of the preferred embodiment, it will be appreciated by those of ordinary skill in the art that a wide variety of alternate and/or equivalent embodiments or implementations calculated to achieve the same purposes may be substituted for the embodiments shown and described without departing from the scope of the present invention. Those with skill in the art will readily appreciate that embodiments in accordance with the present invention may be implemented in a very wide variety of ways. This application is intended to cover any adaptations or variations of the embodiments discussed herein. Therefore, it is manifestly intended that embodiments in accordance with the present invention be limited only by the claims and the equivalents thereof.

What is claimed is:

1. A vertebral fixation plate, comprising:
    a primary plate body having a cranial-caudal axis, a base region forming an angle of approximately 45°-135° with respect to the cranial-caudal axis of the primary plate body, and at least one securing screw hole configured to accept a securing screw to secure the primary plate body to an anterior surface of a C2 vertebra, wherein the plate body is configured to secure to the C2 vertebra and fix a dens fracture thereof, and wherein the plate body does not span a disk space between vertebrae when installed; and
    at least one interfragmentary screw hole centrally located in the base region and configured to accept an interfragmentary screw having a length to secure the base region to the inferior surface of the C2 vertebra and traverse the dens fracture.

2. The vertebral fixation plate of claim 1, wherein said primary plate body comprises a shoulder region and a waist region, said waist region being coupled at one end to said shoulder region and at an opposite end to said base region, wherein said waist region tapers along at least a portion thereof between said shoulder region and said base region.

3. The vertebral fixation plate of claim 1, wherein said at least one securing screw hole is a locking screw hole.

4. The vertebral fixation plate of claim 1, wherein said at least one securing screw hole comprises at least two securing screw holes.

5. The vertebral fixation plate of claim 4, wherein at least two of said at least two securing screw holes are arranged with predefined screw insertion angles that converge.

6. The vertebral fixation plate of claim 1, wherein said interfragmentary screw hole is a locking screw hole.

7. The vertebral fixation plate of claim 1, wherein at least a portion of the primary plate body has a transverse curvature.

8. A vertebral fixation construct, comprising:
    a vertebral fixation plate having a primary plate body and a base region, said primary plate body having a cranial-caudal axis and at least one securing screw hole, said securing screw hole configured to accept a securing screw to secure the primary plate body to an anterior surface of a C2 vertebra, said base region having an interfragmentary screw hole centrally located in the base region and configured to accept an interfragmentary screw, wherein said base region forms an angle of approximately 45°-135° with respect to the cranial-caudal axis of the primary plate body, wherein the plate body is configured to secure to the C2 vertebra and fix a dens fracture thereof, and wherein the plate body does not span a disk space between vertebrae;
    at least one securing screw configured for insertion into the vertebra via said at least one securing screw hole; and
    an interfragmentary screw configured for insertion into the vertebra via said interfragmentary screw hole, wherein the interfragmentary screw has a length to extend from the base region of the plate body into the dens.

9. The vertebral fixation construct of claim 8, wherein said interfragmentary screw is a fully threaded, variable pitch screw.

10. The vertebral fixation construct of claim 8, wherein said primary plate body comprises a shoulder region and a waist region, said waist region being coupled at one end to said shoulder region and at an opposite end to said base region, wherein said waist region tapers along at least a portion thereof between said shoulder region and said base region.

11. The vertebral fixation construct of claim 8, wherein said at least one securing screw hole is a locking screw hole and said at least one securing screw is a locking screw.

12. The vertebral fixation construct of claim 8, wherein said at least one securing screw hole comprises at least two securing screw holes, and wherein said at least one securing screw comprises at least two securing screws.

13. The vertebral fixation construct of claim 12, wherein at least two of said at least two securing screw holes are arranged with predefined screw insertion angles that converge.

14. The vertebral fixation construct of claim 8, wherein said interfragmentary screw hole is a locking screw hole.

15. The vertebral fixation construct of claim 8, wherein at least a portion of the primary plate body has a transverse curvature.

* * * * *